United States Patent [19]

Pez

[11] 4,024,169

[45] May 17, 1977

[54] TITANIUM COMPLEXES WITH NITROGEN

[75] Inventor: Guido P. Pez, Boonton, N.J.

[73] Assignee: Allied Chemical Corporation, Morris Township, N.J.

[22] Filed: Nov. 28, 1975

[21] Appl. No.: 636,197

[52] U.S. Cl. .................... 260/429.5; 252/431 N; 260/2 M; 260/429 CY; 260/676 R; 260/680 R; 260/683.15 D; 423/352; 423/358

[51] Int. Cl.² .......................................... C07F 7/28

[58] Field of Search ................ 260/429.5, 2 M

[56] References Cited

UNITED STATES PATENTS 3,776,932  12/1973  Pez .......................... 260/429.5 X

OTHER PUBLICATIONS

Bercaw et al., J.A.C.S. 94(4), pp. 1219–1232, (1972).
Shilov et al., J. Chem. Soc., Chem. Comm., p. 1178, (1972).
Shilov et al., Dokl. Akad. Nauk, USSR, vol. 213, (1), p. 116, (1973).
Brintzer et al., J.A.C.S. 94(4), 1233–1238, (1972).
Ungurenasu et al., J. Inorg. Nucl. Chem. V3, pp. 3753–3758, (1972).
Marvich et al., J.A.C.S. 93(8), 2045–2048, (1971).
Tamelen et al., J.A.C.S. 91(6), 1551–1552, (1969).
Brintzinger et al., J.A.C.S. V92(4), 1105–1107, (1970).
Bercaw et al., J.A.C.S., V91(26), 7301–7306, (1969).
Watt et al., J.A.C.S., V92(4), 826–828, (1970).
Cotton, Prog. In Inorg. Chem. V9, 9 to 11, (1968).
Brintzinger et al., J.A.C.S., 92(21), 6182–6185, (1970).
Watt et al., J.A.C.S., 88(6), 1138–1140, (1966).
Salzmann et al., Helve. Chim. Acta., V50, 1831–1836, (1967).

*Primary Examiner*—Helen M. S. Sneed
*Attorney, Agent, or Firm*—Robert A. Harman; Ernest A. Polin

[57] ABSTRACT

Complexes of the titanium cyclopentadienyl compound

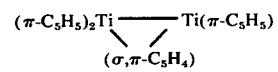

and nitrogen, having the probable structure:

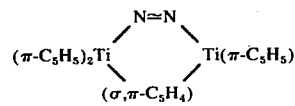

where the symbol N≈N represents a bonding state intermediate between the azo-N=N- bond and the hydrazine =N-N= bond; such complex having the simple dimeric form as indicated by molecular weight determination on this form dissolved in tetrahydrofuran, and having a polymeric form wherein a nitrogen atom of one molecule of the dimeric form is coordinated by a dative link with a Ti atom of another molecule of the dimeric form, as suggested by low solubility of this polymeric form in 1,2-dimethoxyethane and breakdown of this form to the dimeric form by action of tetrahydrofuran.

Another related complex is a black solid nitrogen-containing reaction product of the above titanium cyclopentadienyl compound in dry state with nitrogen at about 60 atmospheres pressure, having an infrared spectrum typical of a metallocene compound with no N-N or Ti-N vibration absorption bands.

The nitrogen in these complexes is reactive, e.g. with reducing agents such as potassium naphthalene, to afford ammonia. Moreover, the complexes are catalytically active for hydrocarbon conversions such as conversion of ethylene to ethane, butane, 1-butene and 1,3-butadiene.

3 Claims, 2 Drawing Figures

TITANIUM COMPLEXES WITH NITROGEN

CROSS-REFERENCE TO RELATED APPLICATION AND RELATED PRIOR ART

In my patent, U.S. Pat. No. 3,776,932 of Dec. 4, 1973, I have described the preparation of cyclopentadienyl titanium compound capable of reacting with molecular nitrogen, e.g., when wet with a nonpolar solvent. A deep blue solution is formed, for example in toluene at −80° C. It slowly loses its blue color evolving molecular nitrogen, upon standing at room temperature. Others have now noted somewhat similar dinitrogen complexes with cyclopentadienyl titanium compounds. These complexes are indicated to have a formula $[(\pi\text{—}C_5H_5)_2Ti]_2N_2$. The dinitrogen moiety in these complexes is indicated to be a link between the two dicyclopentadienyl titanium groups (Bercaw et al., Journal of the American Chemical Society, vol. 94 (1972) page 1219–1238 at page 1226; Shilov et al., Journal of the Chemical Society, Chemical Communications 1972, page 1178).

SUMMARY OF THE INVENTION

I have now found a new class of dinitrogen complexes with the cyclopentadienyl titanium compound of my U.S. Pat. No. 3,776,932 in which the dinitrogen moiety participates with the titanium atoms in a ring structure, by bridging two titanium atoms which are also bridged by a cyclopentadienylene radical, bonded to one titanium atom by a pi bond and to the other by a sigma bond; having the structure:

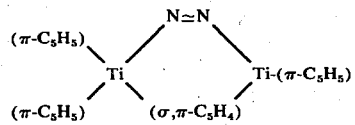

where the symbol N≃N represents a bonding state intermediate between the azo -N=N- bond and the hydrazine =N-N= bond.

Such complexes are obtained in accordance with this invention by contact of the said cyclopentadienyl titanium compound with molecular nitrogen in a polar solvent, in particular, 1,2-dimethoxyethane or tetrahydrofuran. The products are dimeric or polymeric, depending on the conditions. The polymeric form, upon contact with tetrahydrofuran, is broken down to the dimeric form.

The nitrogen in these complexes is reactive, e.g. with reducing agents such as potassium naphthalene to afford ammonia. The dimeric form has been found to be an active catalyst for hydrocarbon conversions; in particular it converts ethylene gas at 1 atmosphere pressure and room temperature to a mixture of ethane, butane, 1-butene and 1,3-butadiene.

A different related complex is obtained by contacting the dry cyclopentadienyl compound with $N_2$ at 60 atm. pressure.

DRAWINGS

The drawings show infrared absorption spectra of complexes of this invention, suspended in n-hexadecane-$d_{34}$.

DETAILED DESCRIPTION

The cyclopentadienyl titanium compound of my U.S. Pat. No. 3,776,932 has been found by use of X-ray diffraction of a single crystal of a bis-tetrahydrofuran derivative, and by infrared spectrum, elemental analysis, and molecular weight determination to have the structure:

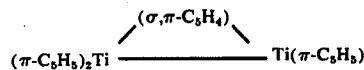

Upon contacting this compound (I) in 1,2-dimethoxyethane (DME) with $N_2$ at 200 psi the blue complex, referred to above, is formed. On standing under $N_2$ pressure the DME solution loses its blue color slowly over a period of 12–16 hours at room temperature, giving a mixture of two phases: (a) a green solution and (b) a black precipitate.

The precipitate was isolated by filtration under $N_2$ and purified by washing sparingly with DME. This product is a new $N_2$ complex of cyclopentadienyl titanium. The following is a summary of the physical and chemical data which suggest the material to be a coordination polymer wherein N of one molecule is coordinated with Ti of another molecule, and as having the structure:

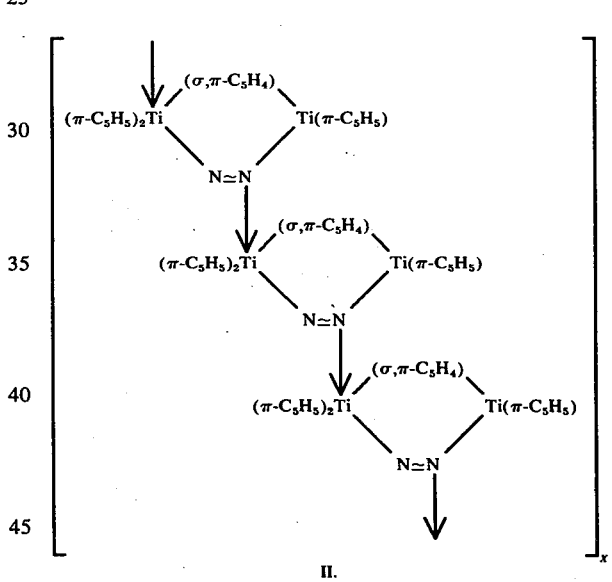

II.

Elemental Analyses

Calcd. for $C_{20}H_{19}Ti_2N_2$: C, 62.6, H, 4.96; N, 7.31; Ti, 25.06. Found: C, 62.80; H, 5.41; N, 7.22; Ti, 24.54 (i.e. reasonably good agreement with that calculated).

Solubility

The compound is very sparingly soluble in DME, indicating that it is very likely a coordination polymer with dative coordination links between nitrogen and titanium.

Infrared Spectrum

Figure 1:
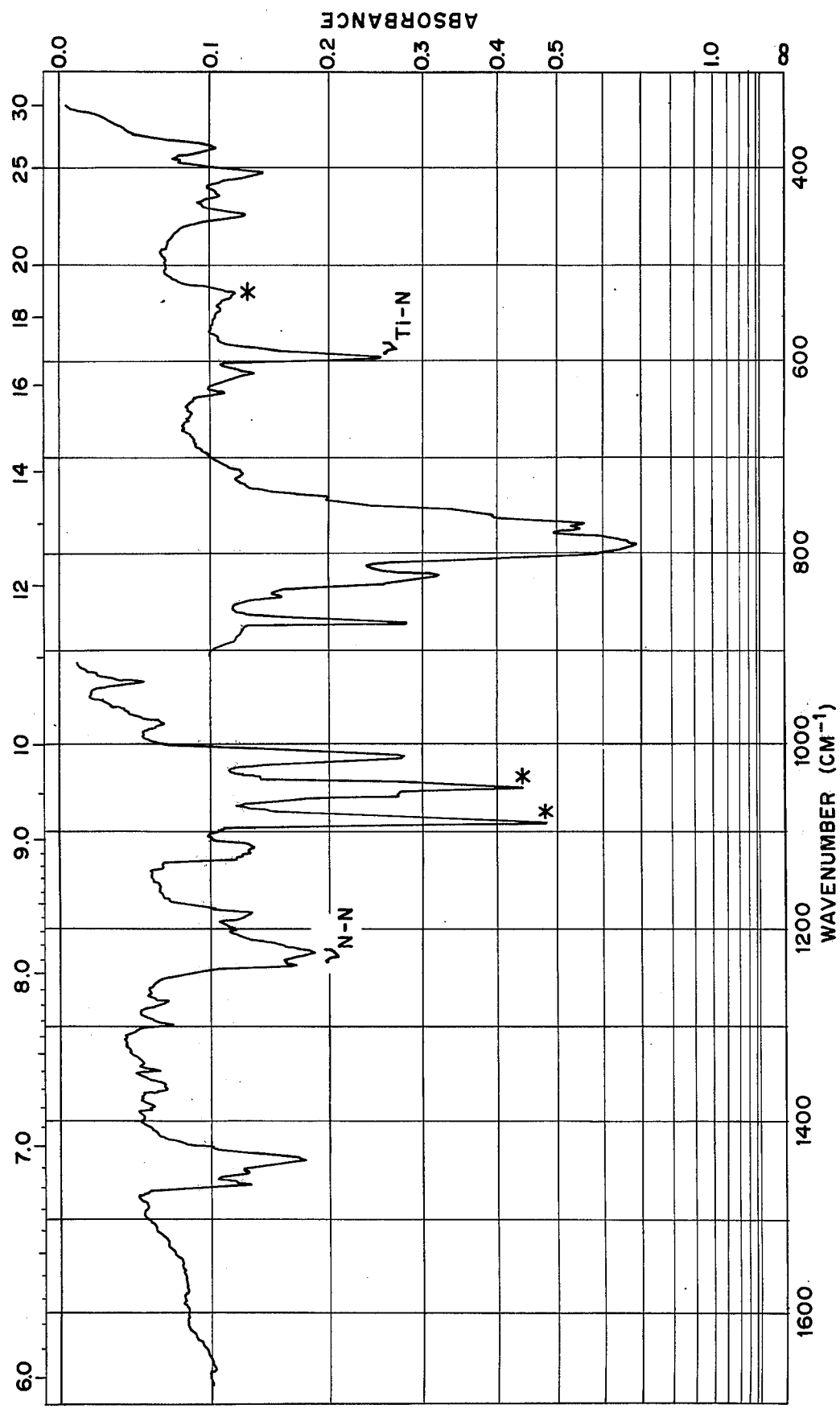

The spectrum (FIG. 1) is that of a typical metallocene system, except that the out-of-plane C-H bending absorption peak at about 790 cm$^{-1}$ displays some fine structure. This structure implies that (at least in the solid state) there are a number of cyclopentadienyl ligands, (i.e. $C_5H_5,C_5H_4$) each in a different physical environment. The peaks marked (*) are due to the n-hexadecane $-d_{34}$ suspension medium (deuterated n-hexadecane). Absorption peaks that arise from nitrogen-nitrogen and metal-nitrogen stretching vibrations have been carefully characterized using $N_2^{14}$ and $N_2^{15}$ isotopes.

| Assignment | Frequency (cm$^{-1}$) |
|---|---|
| $N^{14}-N^{14}$ | $1221.9 \pm 0.3$ |
| $N^{15}-N^{15}$ | $1182.2 \pm 0.3$ |
| Ti—$N^{14}$(anti-sym) | $592.4 \pm 0.3$ |
| Ti—$N^{15}$(anti-sym) | $581.4 \pm 0.5$ |

The N-N value of 1222 cm$^{-1}$ is the lowest N-N stretching vibration frequency that has yet been recorded for a transition metal-dinitrogen complex. (Shilov et al have reported an N-N stretching frequency of 1255 cm$^{-1}$ for the material said to be

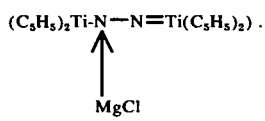

The herein described black polymeric

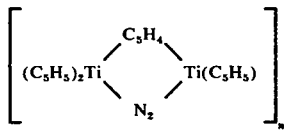

appears to contain a dinitrogen species that has been very greatly modified by coordination onto titanium. Most dinitrogen complexes of the later transition metals have N-N stretching frequencies which range from 1900 to 2200 cm$^{-1}$. The N-N stretching frequency for $N_2$ gas is at about 2300 cm$^{-1}$.

Molecular nitrogen does not form a blue dinitrogen complex with solutions of the above cyclopentadienyl titanium compound in tetrahydrofuran (THF), at least not at pressures less than 300 psi. Instead, $N_2$ and such titanium compound in THF slowly react over 16 hours at 23° C. to form a deep red colored solution. On removal of the THF, a new material of composition $(C_5H_5)_2Ti.N_2.Ti(C_5H_4)(C_5H_5)$ is obtained. The same substance is also formed when the above black polymeric $[(C_5H_5)_2Ti.N_2.Ti(C_5H_4)(C_5H_5)]_n$ is brought into contact with THF. This product is probably a cyclic complex, with bridging $N_2$ and $C_5H_4$, having the formula:

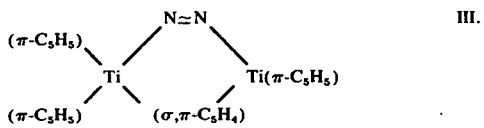

III.

The characterization data, and the physical and chemical properties of this dinitrogen complex are presented below.

Elemental Analyses

Calcd. for $(C_{20}H_{19}Ti_2N_2)$: C, 62.6; H, 4.96; Ti, 25.06; N, 7.31

Found: C, 65.00; H, 5.70; Ti, 23.90; N, 5.33.

These results are only in fair agreement with the proposed composition. The high carbon and low nitrogen values probably result from contamination by the reaction solvent viz. tetrahydrofuran, and with the starting cyclopentadienyl titanium compound. Traces of THF solvent are visible in infrared spectra of the new compound.

Molecular Weight Measurements

Molecular weight determinations were done in tetrahydrofuran, using an isopiestic method. The values obtained: 372, 372 and 346 are in good agreement (-3%, -3%, -10%) with the above cyclic dimeric formulation (M.W. = 383).

Infrared and Raman Spectra

Figure 2:
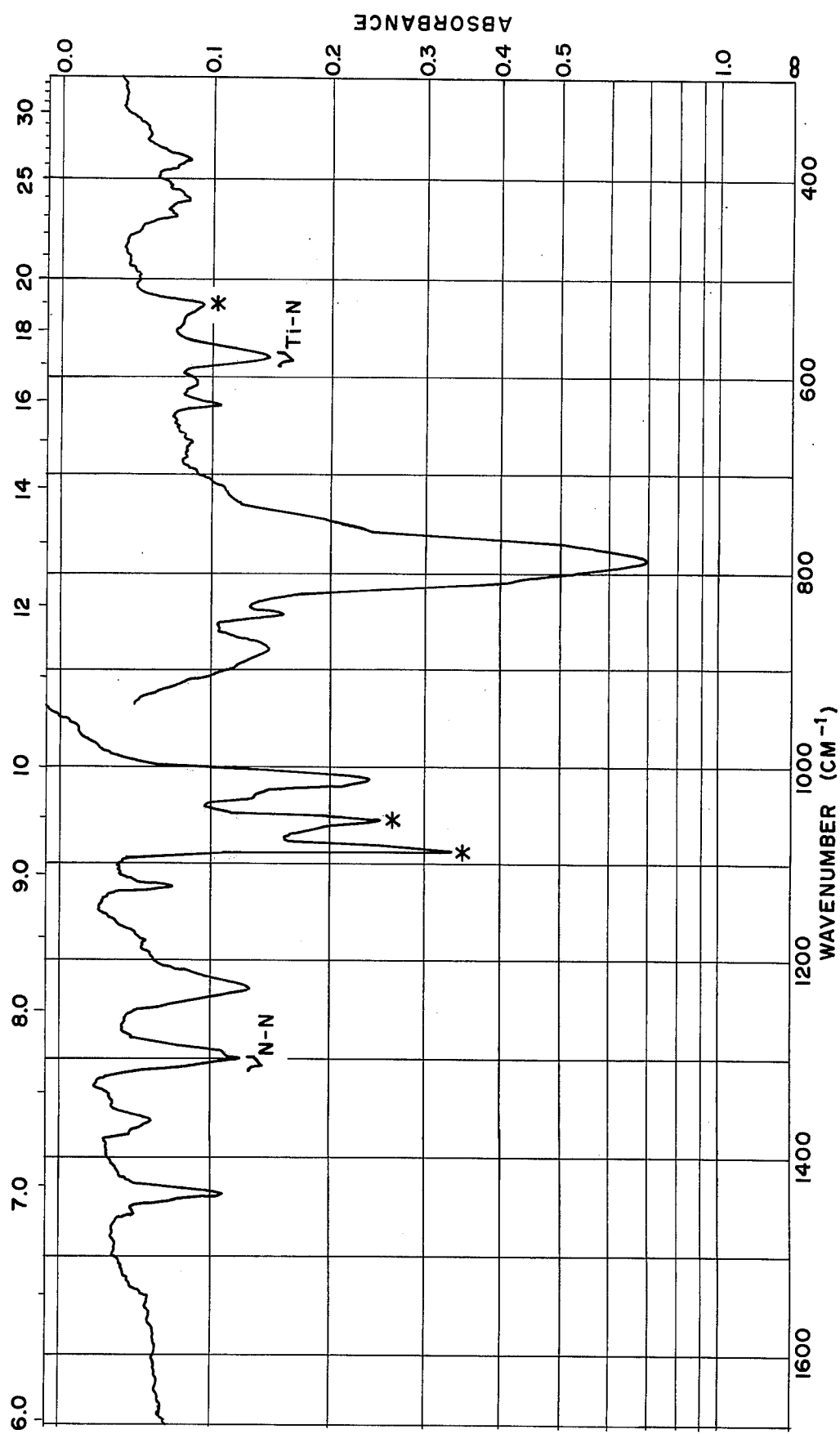

The infrared spectrum of the above red-brown complex (III) is also typical of that of a metallocene. See FIG. 2. In addition to the ($C_5H_5$) ligand vibrations at frequencies of 3080 cm$^{-1}$ (C-H stretch), 1010 cm$^{-1}$ (in-plane CCH bend) and 790 cm$^{-1}$ (out-of-plane CH bend), vibrations from N-N and Ti-N stretching are evident. The latter modes are also visible in the Raman effect. The vibrational frequency assignments for the nitrogen-related fundamentals are given below:

| Assignment | Infrared | Raman |
|---|---|---|
| | cm$^{-1}$ | cm$^{-1}$ |
| $N^{14}-N^{14}$ | 1296.0 | 1298, 1304 |
| $N^{15}-N^{15}$ | 1252.1 | 1259 |
| Ti—$N^{14}$ (anti-sym.) | 581.4 | 579 |
| Ti—$N^{15}$ (anti-sym.) | 566.4 | 565 |
| Ti—$N^{14}$ (sym.) | — | 526 |
| Ti—$N^{15}$ (sym.) | — | 509 |

There is little doubt that in this complex, the $N_2$ is in a considerably reduced form and falls somewhere between an "azo" -N=N- and a "hydrazine-like" =N-N= structure. The N-N vibration for azobenzene occurs at frequency of 1441 cm$^{-1}$, while the N-N vibration for hydrazines occurs at about 1000 cm$^{-1}$.

Chemical Properties a. Chemical Stability

The above identified $N_2$ complex (III) is stable for at least one day at room temperature as a solid and in solution in electron donor solvents, e.g., THF, DME, triethylamine, N,N,N',N'-tetramethylethylene diamine. In non-polar solvents, (e.g. toluene) the complex turns green without evolution of $N_2$. No attempt was made to characterize the latter product which is presumably yet another $N_2$ complex. It is clear that the metal atoms in the red-brown complex (III) require further saturation for the complex to be stable in solution. This finding is in accordance with what might be expected, if the 18-electron rule is applied to the system. This rule states the most stable structures are those which have an 18-electron or inert gas configuration about the metal atom.

b. Thermal Stability

A sample of the red-brown complex in tetrahydrofuran was refluxed under 1 atm. of $N_2$ gas at about 70° C. for 3 was refluxed under 1 atm. of $N_2$ gas at about 70° C. for 3 hours. The solid was recovered from the THF solution and analyzed for N. Found, % N= 5.92 in contrast to % N= 6.33 for the starting material. It thus appears that very little $N_2$ loss occurs when the complex is heated in THF.

c. Chemical Reduction to $NH_3$

A sample of the red-brown complex was contacted with a six-fold excess of potassium naphthalene in THF for 24 hours under vacuum. After hydrolysis with aqueous HCl, 0.35 moles of $NH_3$ per 1 g-atom of titanium were collected. Thus, the $N_2$ in this complex is reducible. This is probably not the maximum amount of ammonia which could have been collected from the test.

Reaction Product of Dry Compound I, With Nitrogen under Pressure

Finely powdered dry cyclopentadienyl compound (I) was contacted with $N_2$ gas at 900 psi pressure for 3 days at room temperature. After release of the $N_2$ pressure the sample was evacuated and transferred into an ambient argon atmosphere. The product, a black powder (IV), was found to have a nitrogen content of 5.08%. The infrared spectrum of compound (IV) is a typical metallocene spectrum identical to that of compound (I). There are no absorption bands that might be ascribable to N-N or Ti-N vibrations.

This solid compound (IV) dissolves in THF to give a bright green solution, which is stable for at least one day at 25° C. However, in DME, the initially formed green solution turns to a red-brown color within 15 hours and in the process evolves ca. 50% of its bound $N_2$. These solutions in THF or DME clearly do not correspond to any of the $N_2$ complexes above referred to, prepared in these solvents. This reaction product (IV) from solid compound (I) and $N_2$ is probably a centrosymmetric species since no bands ascribable to N-N stretching vibrations are observed.

This compound (IV) catalyzes conversion of ethylene gas at 400 psi pressure and room temperature, under 50 psi of nitrogen, to a mixture of ethane, butane, 1-butene and 1,3-butadiene.

I claim:

1. Complex of the titanium cyclopentadienyl compound

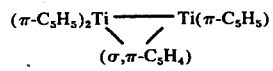

and nitrogen, having the structure:

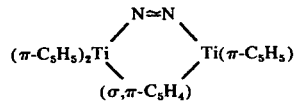

where the symbol $N \rightleftharpoons N$ represents a bonding state intermediate between the azo-N=N- bond and the hydrazine =N-N= bond; such complex having a cyclic dimeric form as indicated by molecular weight determination on this form dissolved in tetrahydrofuran, and having a polymeric form wherein a nitrogen atom of one molecule of the cyclic dimeric form is coordinated with a Ti atom of another molecule of the cyclic dimeric form as indicated by low solubility of this polymeric form in 1,2-dimethoxyethane and breakdown of this form to the cyclic dimeric form by action of tetrahydrofuran; said cyclic dimeric form of said complex showing molecular weight in tetrahydrofuran in good agreement with the theoretical value of 383 for such dimeric form, and having the following characteristic vibrational frequency assignments for the $N_2$- related fundamentals:

| Assignment | Infrared | Raman |
| --- | --- | --- |
|  | $cm^{-1}$ | $cm^{-1}$ |
| $N^{14}-N^{14}$ | 1296.0 | 1298, 1304 |
| $N^{15}-N^{15}$ | 1252.1 | 1259 |
| Ti—$N^{14}$ (anti-sym.) | 581.4 | 579 |
| Ti—$N^{15}$ (anti-sym.) | 566.4 | 565 |
| Ti—$N^{14}$ (sym.) | — | 526 |
| Ti—$N^{15}$ (sym.) | — | 509 | said cyclic dimeric form of the complex being a red brown solid, stable for at least one day at room temperature as a solid and in solution in electron donor solvents; said polymeric form of said complex having the following characteristic infrared absorption peaks arising from N-N and Ti-N stretching vibrations:

| Assignment | Frequency ($cm^{-1}$) |
| --- | --- |
| $N^{14}-N^{14}$ | $1221.9 \pm 0.3$ |
| $N^{15}-N^{15}$ | $1182.2 \pm 0.3$ |
| Ti—$N^{14}$(anti-sym) | $592.4 \pm 0.3$ |
| Ti—$N^{15}$(anti-sym) | $581.4 \pm 0.5$ | said polymeric form being a black solid and being very sparingly soluble in 1,2-dimethoxymethane.

2. A red-brown cyclopentadienyl titanium/dinitrogen complex of claim 1 in cyclic dimeric form having an infrared absorption peak attributable to N-N stretching at a frequency of about 1296 wavenumbers ($cm^{-1}$).

3. A black cyclopentadienyl titanium/dinitrogen complex of claim 1 in a polymeric form, having an infrared absorption peak attributable to N-N stretching at a frequency of about 1222 wavenumbers ($cm^{-1}$).

* * * * *